United States Patent
Sugaya et al.

(10) Patent No.: US 9,095,573 B2
(45) Date of Patent: Aug. 4, 2015

(54) METHOD OF BIASING IMPLANTED HUMAN NEURAL STEM CELLS AWAY FROM DIFFERENTIATION INTO GLIAL CELLS BY (+)PHENSERINE TO MODULATE THE CONCENTRATION OF SOLUBLE βAPP IN TISSUE OR CSF

(75) Inventors: Kiminobu Sugaya, Winter Park, FL (US); Amelia Marutle, Orlando, FL (US); Young Don Kwak, Oviedo, FL (US)

(73) Assignee: University of Central Florida Research Foundation, Inc.

( * ) Notice: Subject to any disclaimer, the term of this patent is extended or adjusted under 35 U.S.C. 154(b) by 197 days.

(21) Appl. No.: 11/461,631

(22) Filed: Aug. 1, 2006

(65) Prior Publication Data

US 2007/0071731 A1    Mar. 29, 2007

Related U.S. Application Data

(60) Provisional application No. 60/704,319, filed on Aug. 1, 2005.

(51) Int. Cl.

| | |
|---|---|
| *A61K 48/00* | (2006.01) |
| *A01N 63/00* | (2006.01) |
| *C12N 5/00* | (2006.01) |
| *C12N 5/079* | (2010.01) |
| *C12N 5/0797* | (2010.01) |
| *C12N 5/0735* | (2010.01) |
| *C12N 5/074* | (2010.01) |
| *C12N 5/071* | (2010.01) |
| *A61K 31/407* | (2006.01) |
| *A61K 35/12* | (2015.01) |

(52) U.S. Cl.
CPC ............ *A61K 31/407* (2013.01); *C12N 5/0623* (2013.01); *A61K 35/12* (2013.01)

(58) Field of Classification Search
CPC ... A61K 31/00; A61K 35/12; C07K 14/4711; C12N 5/0623; C12N 5/0662
See application file for complete search history.

(56) References Cited

U.S. PATENT DOCUMENTS

| | | | | |
|---|---|---|---|---|
| 6,497,872 | B1 * | 12/2002 | Weiss et al. | 424/93.1 |
| 6,777,233 | B2 * | 8/2004 | Carpenter | 435/368 |
| 7,153,882 | B2 * | 12/2006 | Greig et al. | 514/411 |
| 2003/0139410 | A1 | 7/2003 | Sugaya et al. | |
| 2003/0148513 | A1 | 8/2003 | Sugaya et al. | |
| 2003/0219898 | A1 | 11/2003 | Sugaya et al. | |
| 2004/0024043 | A1 | 2/2004 | Greig et al. | |
| 2004/0138282 | A1 * | 7/2004 | Greig et al. | 514/411 |

OTHER PUBLICATIONS

't Hart et al. Curr. Opin. Neurol. 2003. 16: 375-383.*
Taylor et al. Science 2002. 296: 1991-1995.*
Ostenfeld et al. Recent Adv. In Stem cell biology, Adv. Tech. Stand. Neurosurg. 2003.28: 3-89.*
Brannen C, et al., "In vitro differentiation of multipotent human neural progenitors in serum-free medium", 2000, Neuroreport, vol. 11, pp. 1123-1128.
Calhoun M, et al., "Neuronal overexpression of mutant amyloid precursor protein results in prominent deposition of cerebrovascular amyloid", 1999, Proc Natl Acad Sci, vol. 96, pp. 14088-14093.
Kwak YD, et al., "Amyloid precursor protein regulates differentiation of human neural stem cells", 2006, Stem Cells Dev, vol. 15, pp. 381-389.
Sturchler-Pierrat C, et al., "Two amyloid precursor protein transgenic mouse models with Alzheimer disease-like pathology", 1997, Proc Natl Acad Sci, vol. 94, pp. 13287-13292.
Hutchinson, P.J. et al., "Increases in GABA concentrations during cerebral ischaemia: a microdialysis study of extracellular amino acids", 2002, J Neurol Neurosurg Psychiatry, vol. 72, pp. 99-105.
Cirrito, John R et al., "In Vivo Assessment of Brain Interstitial Fluid with Microdialysis Reveals Plaque-Associated Changes in Amyloid-B Metabolism and Half-Life,"Oct. 2003, The Journal of Neuroscience, vol. 23(26), pp. 8844-8853.
Dobrowolska, Justyna A. et al., "Diurnal Patterns of Soluble Amyloid Precursor Protein Metabolites in the Human Central Nervous System", PLOS One, Mar. 2014, vol. 9, Issue 3, 12 pgs.
Toyama, Hiroshi et al., "PET imaging of brain with the B-amyloid probe[11C]6-OH-BTA-1, in a transgenic mouse model of Alzheimer's disease" May 2005, European Journal of Nuclear Medicine and Molecular Imaging, vol. 32, No. 5, pp. 593-600.
"App-amyloid beta (14) precursor protein", Genetics Home Reference, May 2012, ghr.nlm.nih.gov/gene/APP, 5 pages.

* cited by examiner

*Primary Examiner* — Chang-Yu Wang
(74) *Attorney, Agent, or Firm* — Timothy H. Van Dyke; Beusse, Wolter, Sanks & Maire, P.A.

(57) ABSTRACT

Disclosed herein are methods and materials for promoting neurogenesis of endogenous and transplanted stem cells. Specifically exemplified herein are methods that comprise transplanting neural stem cells in conjunction with a regimen of (+)phenserine treatment.

6 Claims, 7 Drawing Sheets

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gagacacctg gggatgagaa                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cttgacgttc tgcctcttcc                                              20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cacactgtgc ccatctacg                                               19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccatctcttg ctcgaagtcc                                              20
```

METHOD OF BIASING IMPLANTED HUMAN NEURAL STEM CELLS AWAY FROM DIFFERENTIATION INTO GLIAL CELLS BY (+)PHENSERINE TO MODULATE THE CONCENTRATION OF SOLUBLE βAPP IN TISSUE OR CSF

RELATED APPLICATIONS

This application claims the benefit of U.S. Provisional Patent application Ser. No. 60/704,319, filed Aug. 1, 2005, incorporated herein by reference.

BACKGROUND

Patients currently suffering from neurodegenerative conditions such as Alzheimer's and Parkinson's have limited treatment options. Conventional drug therapy helps delay or reduce the symptoms of disease but is unable to restore complete functionality of the brain or repair damaged tissue. Through stem cell-based therapies, scientists aim to transplant cells in order to regenerate damaged tissue and restore proper function. However, the inventors have realized that the ability of implanted cells to migrate properly to a desired locus and to differentiate into a desired cell type are fundamental and vital obstacles for implementing in cell transplantation therapy. The inventors have made important strides in addressing such issues.

BRIEF DESCRIPTION OF THE DRAWINGS

FIG. 4. Immunohistochemical analysis of transplanted HNSC expressing immunoreactivity for GFAP and Brdu after 6 weeks differentiation in hippocampal regions of 6-7 months old APP23 and non-transgenic mice that were treated with either saline or phenserine (25 mg/kg). All values are expressed as mean±S.E.M. (n=6-7 within each group), and were obtained by averaging counts of immunoreactive human-specific astroglial cells in the (A) CA1, (B) CA2 and (C) dentate gyrus, measured bilaterally on four to six alternate sections for each mouse. ‡‡ $p<0.01$ indicates a significant difference within saline treated group (Student's unpaired t-test); (D) Correlation of APP protein levels with number of GFAP+/Brdu+ cells in the hippocampus of 6-7 months old APP23 mice that received saline only. Each point corresponds to average APP protein levels and number of GFAP+/Brdu+ cells in the CA1, CA2 and dentate gyrus regions of each individual mouse. (Linear regression r=0.47; $p<0.05$).

DETAILED DESCRIPTION

In reviewing the detailed disclosure which follows, and the specification more generally, it should be borne in mind that all patents, patent applications, patent publications, technical publications, scientific publications, and other references referenced herein are hereby incorporated by reference in this application, in their entirety to the extent not inconsistent with the teachings herein.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

The administration of cholinesterase inhibitors such as (−)Phenserine is believed to be useful in treating cognitive disorders such as Alzheimers disease. The potential positive effects of administering cholinesterase inhibitors is somewhat offset by undesired and potentially dangerous side effects. The administration of cholinesterase inhibitors is believed to increase acetylcholine levels in the brain, which is depleted in an Alzheimers brain, and therefore increase activity of the brain's cholinergic system. However, such inhibitors produce a toxicity caused by their inhibition of acetylcholinesterase, such as nausea, vomiting, dizziness, tremors, bradycardia, inter alia. Some in the field have tried using an enantiomer of (−) phenserine in an effort to avoid some of these undesired side effects. For example, Greig et al., U.S. Patent Pub. 2004/0024043 AND 2004/0138282 discuss use of (+) phenserine which lacks cholinesterase activity, avoiding the side effects of the cholinesterase inhibitors. Grieg et al. demonstrated that administration of (+) phenserine dramatically reduces βAPP levels in the brain. It is believed that this lowering of βAPP levels in the brain in turn results in lowered Aβ levels. Aβ is believed to induce progressive neurodegenerative condition leading to loss of memory characterized by the appearance of senile plaques that are primarily composed of an Aβ and neurofibrillary tangle aggregates.

The focus of the Greig et al. studies is the dramatic reduction of Aβ, thus, one is lead to strive toward shutting down βAPP production as much as possible. The inventors postulate that controlling βAPP rather than shutting down βAPP levels is what is critical in optimizing brain conditions to prevent progression of Alzheimer's disease. Indeed, the inventors surmise that the shutting down βAPP production is counterproductive; it may put a patient in a transient improved state, but it will ultimately lead to a worsened state of progression of the disease. This is discussed further below.

The brain harbors stems cells which require signals to migrate to an area of need. βAPP is a primary inducer of stem cell migration in the brain. The inventors have found that a high concentration of βAPP in the brain will bias differentiation of neural stem cells into astrocytes. Thus, one of the potential pathological bases for the progression of Alzheimer's disease is the exhaustion of endogenous stem cell reserves in Alzheimer's brains which are differentiated into an over abundance of astrocytes as opposed to new neurons. The inventors have also discovered that controlling βAPP levels in the brain to optimal levels is also critical when implementing cell transplantation strategies. As with endogenous sources of stems cells, transplanted stem cells will also be biased to produce undesired glial producing cells, such as astrocytes. Thus, in one embodiment, the invention pertains to a method of transplanting human neural stem cells in the brain in conjunction with a regimen of (+)phenserine treatment. (+)Phenserine may be administered a week to several weeks prior to cell transplantation, and/or a week to weeks subsequent to cell transplantation. Though generating an environment of the brain with reduced levels of βAPP is desired for cell transplantation therapies, generating extremely low levels of βAPP will inhibit cell mobilization which is needed for implanted cells to migrate to their needed location, grow and differentiate in the desired phenotype.

Accordingly, in a preferred embodiment, (+)phenserine is administered in conjunction with human neural stem cell transplantation according to a regimen (dosage amount and frequency) such that the site of transplantation comprises an average βAPP concentration of about 0.5 to about 40 nanograms of βAPP per milliliter of tissue or cerebrospinal fluid. Preferably, the regimen is such that an average βAPP concentration of about 1 to 10 nanograms/ml is maintained over a period of at least one day, two days, one week, two weeks, one month, two months, three months, four months, five months, six months or one year.

U.S. Patent Application Nos. 2003/0219898, 2003/0148513, and 2003/0139410 are incorporated by reference to the extent they are not inconsistent with the teachings herein. The first two of these patent applications describe multiple uses of increased potency cells obtained from the taught methods, and in particular, the implantation of stem cells for different therapeutic treatments of neurological trauma and degenerative conditions. The third patent application is directed to the use of certain compounds to stimulate proliferation and migration of stem cells. Those skilled in the art will readily appreciate that the cells of the present invention could be obtained, or their effectiveness enhanced, by combining with the teachings of the aforementioned patent applications, without undue experimentation. Human neural stem cells may be derived from embryonic or adult allogenic or autogenic sources and may be genetically engineered to be biased to differentiate into a desired phenotype. See for example, co-pending U.S. application Nos. 60/621,483, 60/621,902, and 60/621,901

EXAMPLE 1

Modulation of Human Neural Stem Cell Differentiation in APP23 Transgenic Mice by Phenserine Treatment Materials and Methods
Human Neural Stem Cell Cultures.

HNSCs originally isolated from 9 weeks old fetal cortical tissue were purchased from BioWhittaker (Walkersville, Md.) and the cells were expanded and passaged in a serum-free culture medium, as described in detail previously (Brannen and Sugaya, 2000). Briefly, HNSCs were cultured in 20 ml serum-free supplemented growth medium consisting of Ham's F12/DMEM (Gibco, Burlington, ON), EGF (20 ng/ml, R & D Systems), FGF (20 ng/ml, R & D Systems, Minneapolis, Minn.), B27 (1:50, Gibco), heparin (5 μg/ml, Sigma, St. Louis, Mo.) and antibiotic-antimycotic mixure (1:100, Gibco) at 37° C. in a 5% humidified incubation chamber (Brannen and Sugaya, 2000). Prior to transplantation, HNSCs were incubated with 3 μM bromo-deoxyuridine (BrdU, Sigma) for 48 hr to label cell nuclei to distinguish them from the host cells.

Animals.

APP23 mice, expressing the 751-amino acid human amyloid-precursor protein (hAPP751) with the Swedish double mutation (K670N, M671L) driven by the neuron-specific murine Thy-1-promoter (Sturchler-Pierrat et al., 1997) were received as a gift from Novartis Pharma Ltd., (Switzerland), and employed to breed a colony of experimental animals by backcrossing to C57/BL6 mice. Mixed genotype groups were housed in standard mouse cages with access to food and water ad libitum, constant room temperature and humidity, during a 12/12 hr light/dark cycle. Genotypes were confirmed by PCR (Calhoun et al., 1999). In all experiments wild-type littermates served as controls. All animal experimental procedures were carried out in compliance with National Institutes Health Guidelines for Care and Use of Laboratory Animals, and approved by the Animal Research Committee (protocol 00-24) at the University of Central Florida.

(+)-Phenserine Treatment.

A total of 55 age and sex-matched APP23 (n=30) and wild-type (n=25) mice (ages ranged from 4-7 months) were administered with either (+)-phenserine (25 mg/kg/day, i.p.) or 0.9% saline (control) for 14 consecutive days. Animals were subsequently divided into two groups that were either sacrificed following 14 days treatment (n=17 APP23 and n=13 wild-type, respectively) or received transplantation of HSNC into the lateral ventricle (n=13 APP23 mice and n=12 wild-type, respectively). (+)-Phenserine or saline injection was continued once a day for 1 week after a 2-day recovery from transplantation surgery. All animals were sacrificed within 12 hrs of receiving the final dose of (+)-phenserine or 0.9% saline by an overdose of a 1:1 mixture of Ketamine (100 mg/kg) and Xylazine (20 mg/kg), and transcardially perfused with phosphate buffer (PBS). Brains were removed, dissected into the hippocampus and cortex, and tissue samples were maintained on dry ice and stored at −80° C. until Western blotting and PCR experiments were performed. For the group of transplanted animals, these were transcardially perfused with PBS and 4% paraformaldehyde (pH 7.4). Brains were removed and post-fixed for 8-12 h in 4% paraformaldehyde, and cryoprotected in 20% sucrose-PBS overnight. The brains were subsequently cut on a cryostat (20 μm coronal sections) and kept in PBS at 4° C. for fluorescent immunohistochemical analysis.

Animal Surgery and Transplantation.

Animals were deeply anesthetized with a 1:1 mixture of Ketamine (100 mg/kg) and Xylazine (20 mg/kg) and mounted onto a stereotaxic apparatus (ASI Instrument, USA). For transplantation, approximately $10^5$ cells HNSCs were suspended in 10 μl PBS, and slowly injected into the right lateral ventricle of each mouse using a 25 μl Hamilton gastight syringe (Hamilton, Reno, Nev., USA) with a 22-gauge beveled needle attached. The tip was held in place for 3 min during delivery and left in place for another 3 min after each injection. Intra-ventricular injection minimizes disruption of brain tissue and may leverage endogenous signals (eg. chemokines released by microglia in response to damage) that might affect stem cell migration. In reference to the bregma, the coordinates used for implantation were as follows: anterior posterior (A/P) −0.6 mm; medial lateral (M/L) +1.0 mm; dorsal/ventral (D/V) +2.4 mm. No immune suppression was utilized and all efforts were made to minimize the number of animals used and their suffering by observation of maintained body weight and also by monitoring incisions for swelling and proper healing of the incision site.

Protein Isolation and Western Blot Analysis.

Western blot analysis was performed to analyze effect of (+)-phenserine on the relative APP and GFAP protein expression in APP23 and control mice. Dissected tissues from the cortex and the hippocampus of (+)-phenserine and saline treated animals were homogenized in ice-cold lysis buffer containing 1% NP40, 150 mM NaCl, 50 mM Tris (pH 8.0), and 1× protease inhibitor cocktail (Roche Diagnostics, Indianapolis, Ind.). The homogenates were centrifuged and washed twice at 12,000× g for 10 min at 4° C. and the supernatants were used for protein quantification by the Bradford method using Bio-Rad Protein Assay Dye Reagent (Bio-Rad, Hercules, Calif.). Samples were denatured in a sample buffer (Invitrogen, Carlsbad, Calif.) for 10 min at 70° C. Fifteen μg of protein was loaded per well and proteins separated under non-reducing conditions on NuPAGE 4-12% Novex Bis-Tris gels (Invitrogen) for 60 min at 200 V, and then blotted onto PVDF membranes (Bio-Rad) for 120 min at 30 V. For the detection of APP and GFAP protein, membranes were blocked in phosphate buffered saline, pH 7.4, and 0.05% Tween-20 (PBS-T), with 5% non-fat dried milk and thereafter incubated with mouse monoclonal anti-Alzheimer precursor protein (22C11) A4 antibody (1:1000, Chemicon, Temecula, Calif.) and rabbit anti-GFAP antibody (1:1000, Promega, Madison, Wis.) in PBS-T containing 1% non-fat dried milk over night at 4° C. To standardize the amount of protein loaded on to each gel, the polyclonal rabbit anti-B-actin antibody (1:1000, Cell Signaling Technology, Danvers, Mass.) was used. The membranes were washed three times for 15 min in PBS-T and then incubated with secondary horseradish peroxidase-conjugated antibodies (anti-mouse IgG and anti-rabbit IgG, Jackson Immunoresearch Laboratories Inc, West Grove, Pa.) at RT for 1 hr. Three final washes of 15 min in duration each were performed. Signals were visualized by incubation of the membranes in ECL Plus reagents (Amersham Biosciences, Buckinghamshire, UK), exposed to Hyper Performance Chemiluminescence film (Amersham) and developed according to standard procedures. The films were scanned and the optical density of each specific band relative to β-actin, was analyzed by the public domain NIH Image J software (version 1.33u) and expressed in means±SD from experiments performed in triplicate.

Real Time RT-PCR Analysis.

Total RNA from hippocampal and cortical tissues from each animal treated with either (+)-phenserine or saline was isolated with Trizol reagent (Invitrogen) according to the manufacturer's protocol. One μg of the total RNA was transcribed into cDNA with reagents from the iScript cDNA Synthesis Kit (Bio-Rad). Complete reaction mixture was prepared according to kit instructions and incubated at 42° C. for 30 min, 85° C. for 5 min and then cooled. Relative quantification with Real-time PCR was determined using the MyiQ Real-Time PCR Detection System Software (Bio-Rad), and reactions were performed in a thermal iCycler using the Bio-Rad MyiQ IQ SYBR Green Supermix (Bio-Rad) according to the following conditions; denaturation of cDNA for 5 min at 94° C.; amplification (40 cycles) for 30 sec at 94° C., annealing at 56° C. for 30 sec, and extension at 72° C. for 30 sec, with a final extension at 72° C. for 5 min. The authenticity of the PCR products was verified by melt-curve analysis at 55° C. to 95° C. for 10 sec and cooling for 5 min at 20° C. The primers used in this experiment were: APP (forward) 5'-GAGACACCTGGGGATGAGAA-3' (SEQ ID NO: 1, APP (reverse) 5'-CTTGACGTTCTGCCTCTTCC-3' (SEQ ID NO: 2, β-actin (forward) 5'-CACACTGTGCCCATC-TACG-3' (SEQ ID NO: 3, β-actin (reverse) 5'-CCATCTCT-TGCTCGAAGTCC-3' (SEQ ID NO: 4). The PCR efficiencies of the PCR reactions were evaluated from dilution series of cDNA in real-time PCR. Threshold cycle (Ct) values were used to plot a standard curve in which Ct decreased in linear proportion to the log of the template copy number. A comparative Ct method was then utilized to determine relative expression ratios of APP and β-actin mRNA in samples.

Flourescent Immunohistochemistry.

Free floating coronal brain sections (20 μm) were washed briefly in PBS, denatured with 1M HCl for 20 min and neutralized with PBS for 30 min at room temperature (RT), in order to increase the accessibility of the anti-BrdU antibody to the BrdU incorporated in the cell nuclei. The sections were then blocked in PBS containing 0.25% Triton X-100 and 3% Normal Donkey Serum for 1 hr and incubated with sheep polyclonal anti-BrdU (1:1000, Abcam, Cambridge, Mass.) and mouse IgG2b anti-human βIII-Tubulin, clone SDL3D10 (1:2000, Sigma), or rabbit IgG anti-human Glial Fibrillary Acidic Protein (GFAP 1:500, Sigma) diluted in PBS containing 0.25% Triton X-100 and with 3% Normal Donkey Serum overnight at 4° C. After rinsing in PBS-T, sections were incubated with corresponding secondary antibodies (1:500) conjugated with fluorescein (FITC) or rhodamine (TRITC) (Jackson IR Laboratories, Inc.) for 2 hr at RT. After a final wash in PBS-T, sections were mounted and cover slipped with Vectashield with DAPI (Vector Laboratories, Inc., Burlingame, Calif.) for fluorescent microscopic observation.

Microscopy and Analysis of Differentiation.

Cell migration and differentiation in transplanted mice (n=6-7 mice in each group) were quantified by unbiased bilateral counts of number of BrdU positive cells expressing either the neuronal marker, βIII-Tubulin, or the glial marker, GFAP, in the molecular and granule layers of hippocampal CA1, CA2 and dentate gyrus, and motor and sensory regions of the cerebral cortex using a Leica DMRB fluorescent microscope at 400× magnification. Microscopic images were taken with an Axiocam digital camera (Carl Zeiss) mounted on the DMRB and processed using the QIMAGING with Q Capture software (Qimaging Corporation). An average of 4-6 sections were counted for each animal. The number of transplanted cells counted in each section were averaged for each side so that the final numbers represented the mean neuron or astrocyte number per sampling area.

Data and Statistical Analysis.

Data are presented as mean±SEM of different experiments and differences between groups were analyzed with a two-tailed Student's t-test. A simple linear regression test (GraphPad PRISM 3.0) was used to evaluate possible correlations.

Results

Reduced APP protein expresion following (+)-phenserine treatment

Figure 1:
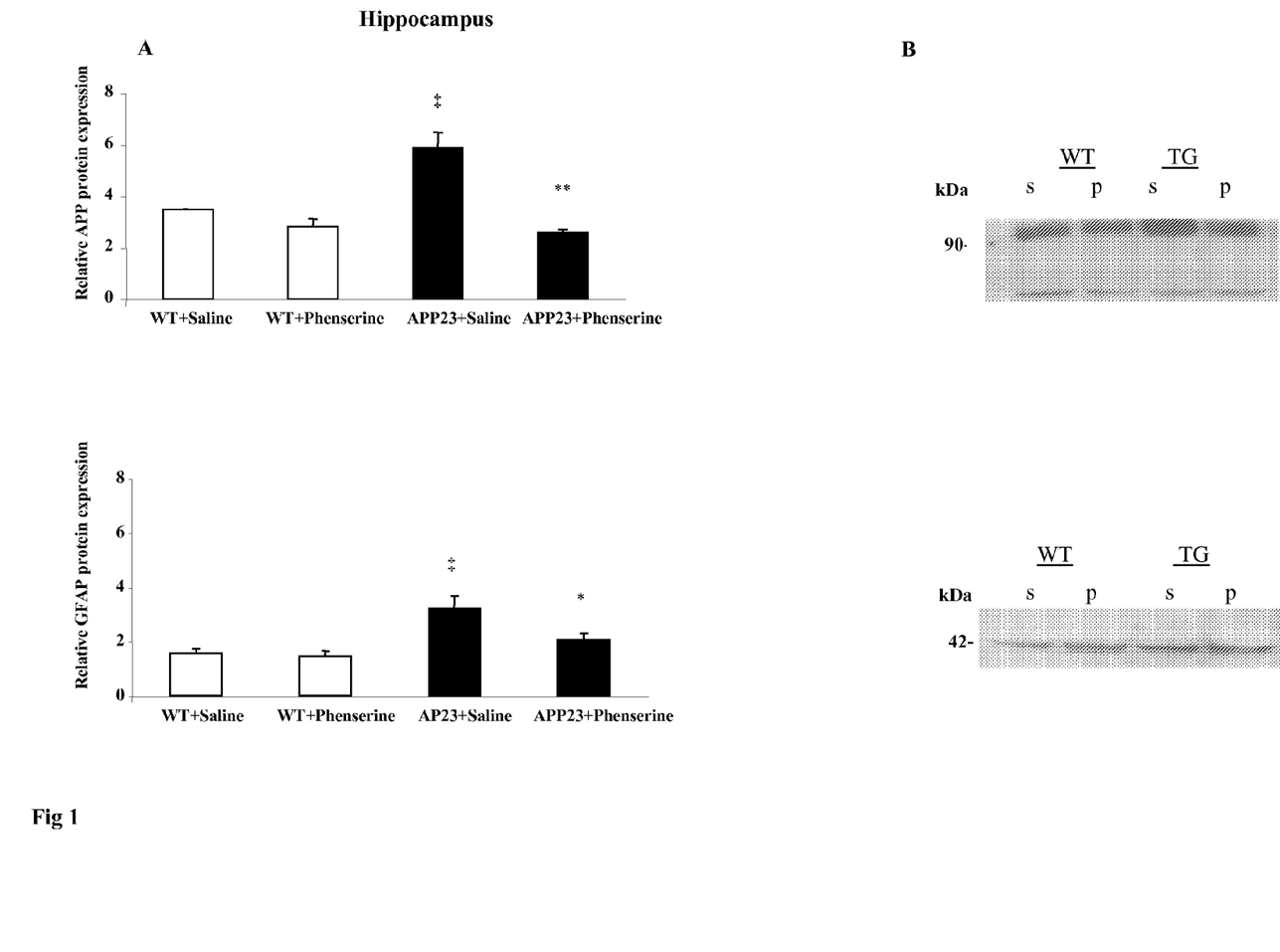
FIG. 1. (A) Relative protein levels of total sAPP (22C11) and GFAP in the hippocampus of 6-8 months old APP23 and non-transgenic mice that were treated with either saline or (+)-phenserine (25 mg/kg) respectively, for 2 weeks. ** $p<0.01$ and * $p<0.05$ indicates significantly different from saline treated. ‡ $p<0.05$ indicates significantly different within saline treated group (Student's unpaired t-test). All values are expressed as mean±S.E.M. from 3-4 independent experiments. (B) Representative Western blots for Sapp and GFAP from saline (s) and (+)-phenserine (p) treated APP23 and non-transgenic mice.

To investigate the effects of (+)-phenserine on APP protein expression, Western blot analysis was performed on cortical and hippocampal tissues from APP23 mice treated with either (+)-phenserine (25 mg/kg, i.p. /day for 14 days) or saline. In agreement with our previous findings, APP23 mice showed significantly ($p<0.05$) higher levels of APP (~2-fold) compared to that of controls (FIG. 1). Following (+)-phenserine treatment, a significant decrease (~3-fold) in APP protein expression was observed in the hippocampus of APP23 mice ($p<0.01$) compared to saline treated mice (FIG. 1). No significant change in APP protein expression was observed between (+)-phenserine treated and saline treated wild-type mice (FIG. 1). Although APP protein expression was also reduced in the cerebral cortices of APP23 and wild-type mice after (+)-phenserine treatment, these reductions did not reach statistical significance ($p>0.05$, data not shown).

Reduced GFAP protein expression following (+)-phenserine treatment

Previous studies have reported that APP overexpression in APP23 mice is also associated with marked gliogenesis in the brains of these mice (Sturchler-Pierrat and Staufenbiel, 2000). Therefore, we also measured GFAP (glial cell marker) expression in these mice and investigated whether treatment with (+)-phenserine could alter expression levels. We observed that APP23 mice had significantly ($p<0.05$) higher (~2.5-fold) GFAP protein expressed in the hippocampus compared to that of wild-type mice. Following (+)-phenserine treatment (25 mg/kg, i.p. /day for 14 days), GFAP expression was significantly ($p<0.05$) reduced (~1.5-fold) in APP23 mice (FIG. 1). No significant changes were observed between (+)-phenserine treated and saline treated wild-type mice (FIG. 1). GFAP protein expression in the cerebral cortices of APP23 and wild-type mice was similar and no significant change was observed after (+)-phenserine treatment (data not shown).

Effect of (+)-phenserine on APP Gene Expression in APP23 Mice

To investigate whether the (+)-phenserine-induced reduction of APP protein expression in APP23 mice was mediated at the transcriptional level, quantitative real-time PCR analysis was performed on cortical and hippocampal tissues from treated animals. However, no significant changes were observed in APP gene expression following (+)-phenserine treatment in both APP23 and wild-type mice (data not shown), indicating that (+)-phenserine reduces APP levels by post-transcriptional processing.

Figure 2:
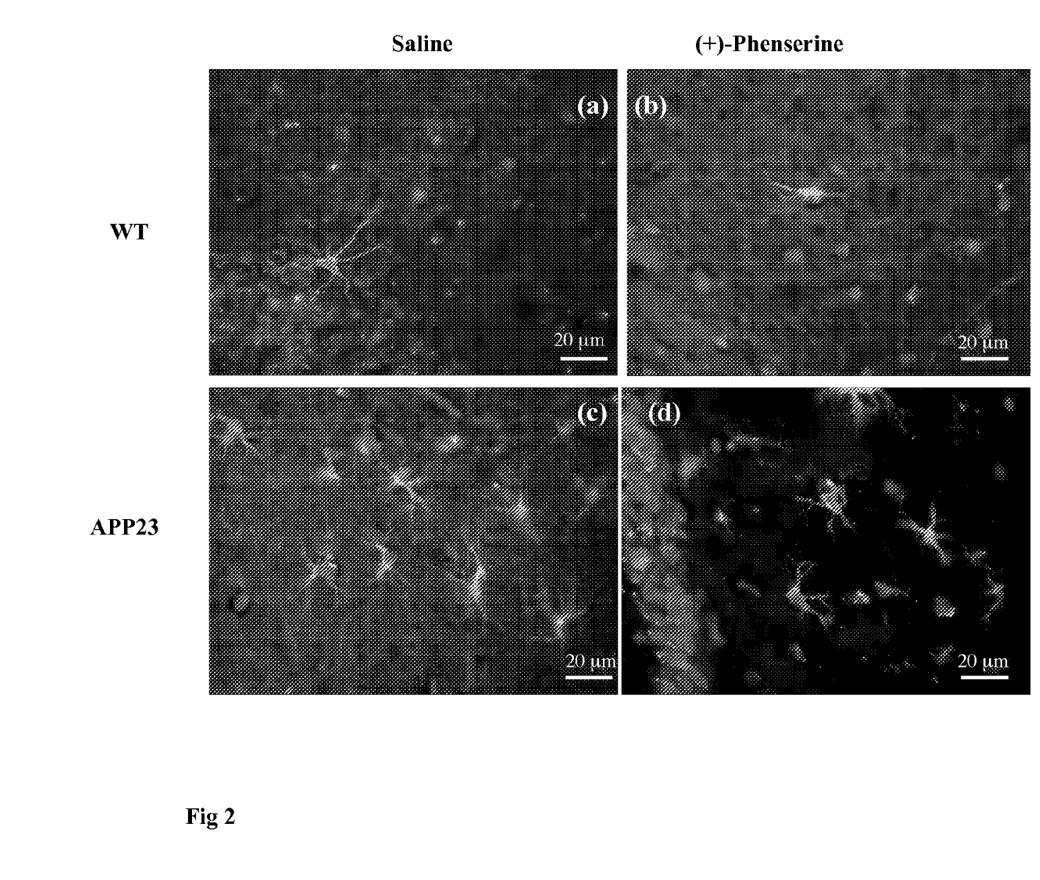
FIG. 2. Differentiation of HNSCs into astroglial cells in vivo after treatment with either saline or (+)-phenserine (25 mg/kg). (a-d) Representative fluorescent immunohistochemical images in the CA1 hippocampal region of 6-7 months old APP23 and non-transgenic mice 6 weeks after HNSCs transplantation. Sections were double-immunofluorescence stained with GFAP (green) and BrdU (red) markers for astroglia cells and donor cells, respectively. All nuclei were counterstained by DAPI (blue).
Figure 3:
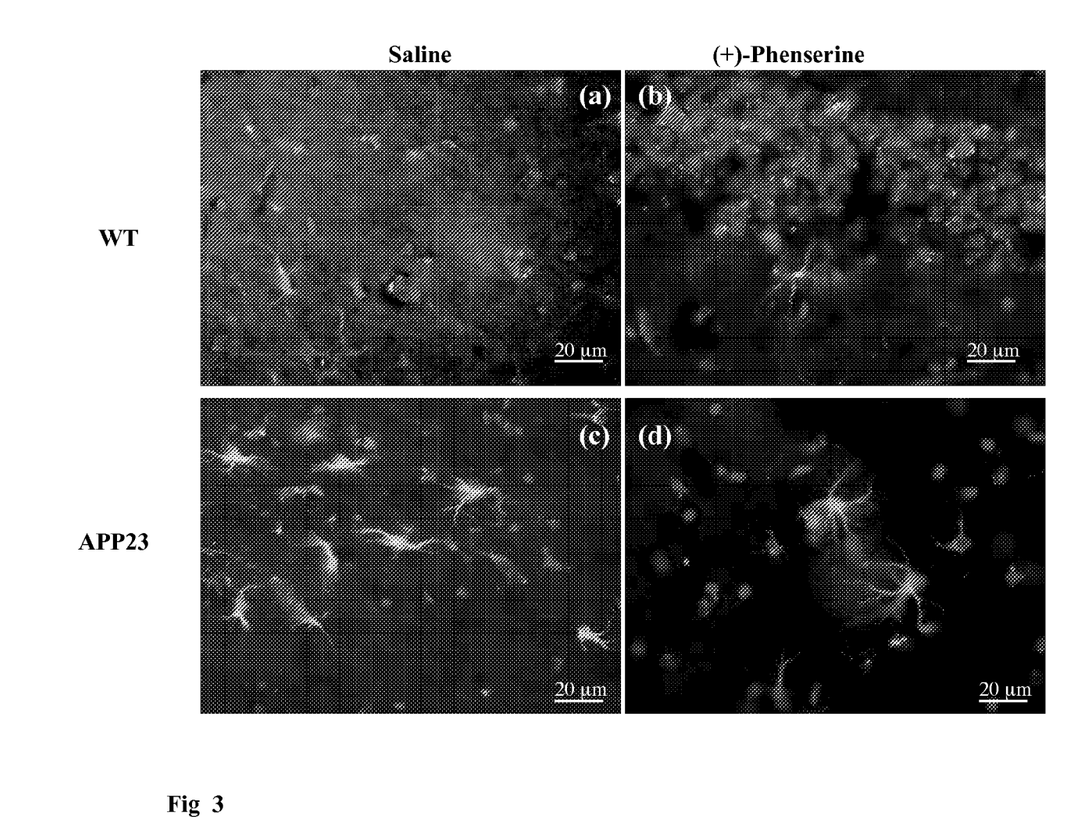
FIG. 3. Differentiation of HNSCs into astroglial cells in vivo after treatment with either saline or (+)-phenserine (25 mg/kg). (a-d) Representative fluorescent immunohistochemical images in the CA2 hippocampal region of 6-7 months old APP23 and non-transgenic mice 6 weeks after HNSCs transplantation. Sections were double-immunofluorescence stained with GFAP (green) and BrdU (red) markers for astroglia cells and donor cells, respectively. All nuclei were counterstained by DAPI (blue).
Figure 4:
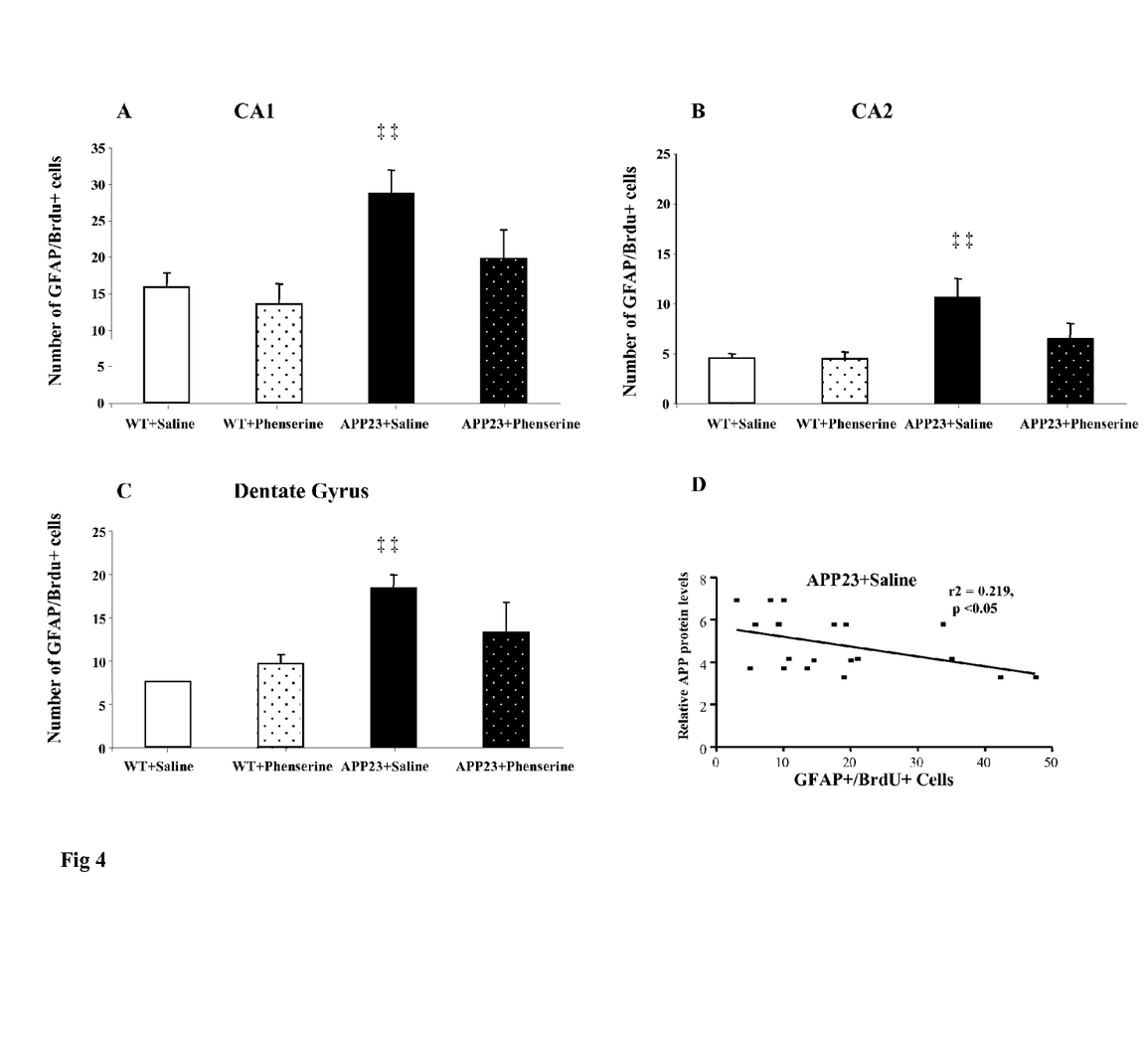

Effects of (+)-phenserine on Glial Differentiation of Transplanted HNSCs in APP23 Mice Six weeks after implantation, fluorescent double label immunohistochemistry was employed to identify cells derived from transplanted HNSCs (BrdU-labeled) and to examine their differentiation into either neural or glial cells. Also, we sought to determine whether the (+)-phenserine-induced effects on APP could influence the differentiation fate of transplanted HNSCs. Transplanted HNSCs survived in vivo and an extensive number of cells exhibiting characteristic astroglial morphologies, and co-expressing BrdU with the astrocytic marker for human GFAP ($BrdU^+/GFAP^+$) were observed in the molecular and granule layers of the hippocampal CA1, CA2 (FIGS. 2-3), and the dentate gyrus (data not shown). Typically, APP23 mice showed more pronounced immunoreactivity for $BrdU^+/GFAP^+$ compared to controls. The cells expressing $BrdU^+/GFAP^+$ in hippocampal regions were counted and the results were expressed as the average number of $BrdU^+/GFAP^+$ cells per region for each treatment group (FIG. 4A-C). APP23 mice showed significantly ($p<0.01$) more $BrdU^+/GFAP^+$ double immuno-positive cells compared to that of wild-type mice (FIG. 4A-C). Following (+)-phenserine treatment, a marked reduction (ranging from 28% to 40%) in number of $BrdU^+/GFAP^+$ double immuno-positive cells was observed in hippocampal regions of APP23 mice (FIG. 4A-C), indicating that (+)-phenserine could reduce the glial differentiation caused by APP over-expression. No significant differences in the number of $BrdU^+/GFAP^+$ double immuno-positive cells were observed in the hippocampus of wild-type mice after (+)-phenserine treatment (FIG. 4A-C). There was a significant correlation ($p<0.05$; linear regression r=0.47) between number of $BrdU^+/GFAP^+$ double immuno-positive cells and APP protein expression in the hippocampus of APP23 mice (FIG. 4D).

Effects of (+)-phenserine on Neuronal Differentiation of Transplanted HNSCs in APP23 Transgenic Mice Examination of neuronal differentiation of transplanted HNSCs was also performed in APP23 and wild-type mice that were treated with (+)-phenserine or saline. The number of cells co-expressing BrdU with the neuronal marker for human β-III tubulin ($BrdU^+/β$-III tubulin$^+$) were counted in the molecular and the granule layers of the hippocampal CA1 and CA2, the dentate gyrus, and in the pyramidal layers of the somatosensory and the motor cortex. To exclude the possibility that measured neuronal immunoreactivity was also detecting non-neuronal and endogenous neurons in mouse that were not derived from the transplanted HNSCs, we stained in parallel experiments sections with the neuronal marker NeuN and a human nuclear specific antibody. Similar results were obtained for NeuN staining as with β-III tubulin and BrdU, thus verifying that the differentiated cells were of human origin (data not shown).

Figure 5:
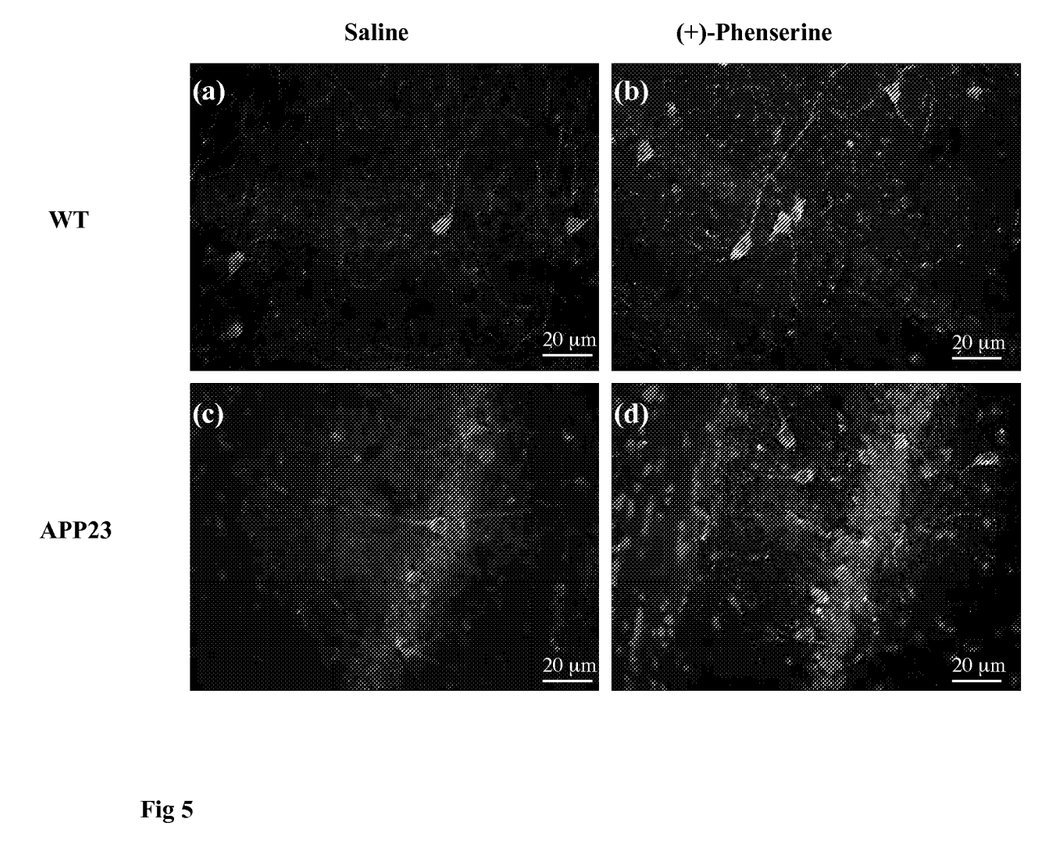
FIG. 5. Differentiation of HNSCs into neuronal cells in vivo after treatment with either saline or (+)-phenserine (25 mg/kg). (a-d) Representative fluorescent immunohistochemical images in the CA1 hippocampal region of 6-7 months old APP23 and non-transgenic mice 6 weeks after HNSCs transplantation. Sections were double-immunofluorescence stained with βIII-tubulin (green) and BrdU (red) markers for neural cells and donor cells, respectively. All nuclei were counterstained by DAPI (blue).
Figure 6:
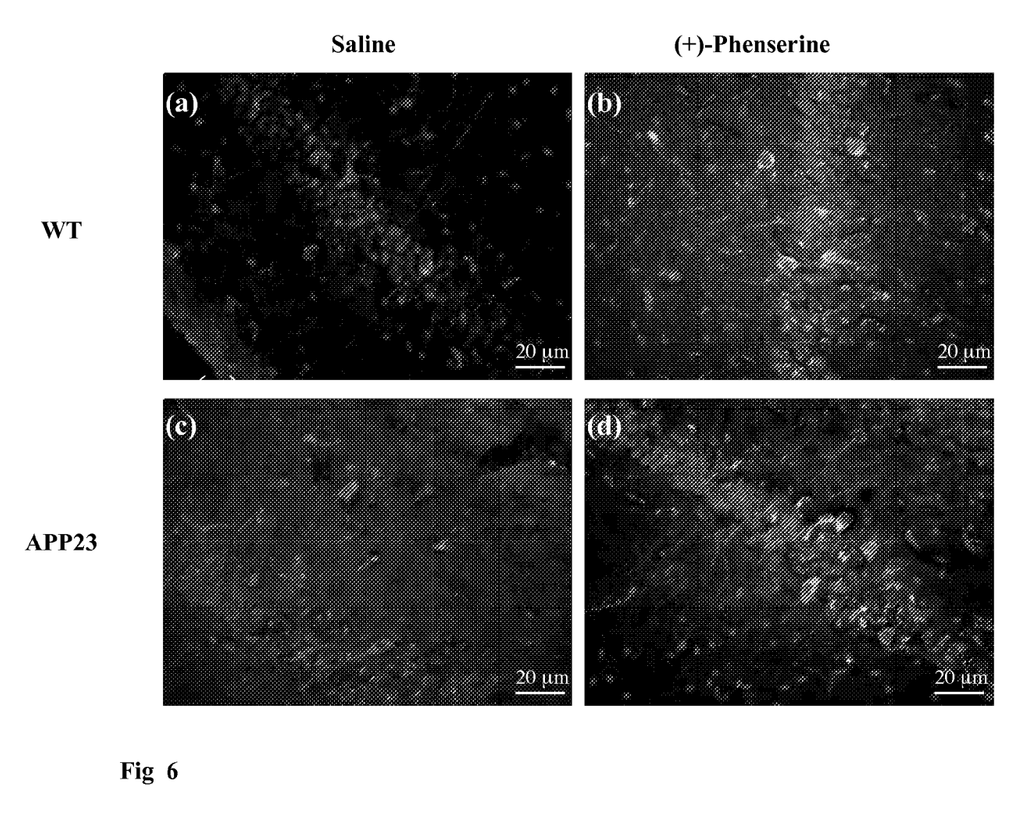
FIG. 6. Differentiation of HNSCs into neuronal cells in vivo after treatment with either saline or (+)-phenserine (25 mg/kg). (a-d) Representative fluorescent immunohistochemical images in the CA2 hippocampal region of 6-7 months old APP23 and non-transgenic mice 6 weeks after HNSCs transplantation. Sections were double-immunofluorescence stained with βIII-tubulin (green) and BrdU (red) markers for neural cells and donor cells, respectively. All nuclei were counterstained by DAPI (blue).

HNSCs transplanted into APP23 and wild-type mice differentiated into β-III tubulin immuno-positive cells. The $BrdU^+/β$-III tubulin$^+$ cells within the CA1 and the CA2 region had large pyramidal morphologies (FIG. 5-6), whereas those in the dentate granule layer displayed a small ovoid appearance typical for dentate granule neurons (data not shown). In the somatosensory and motor cortical regions, $BrdU^+/β$-III tubulin$^+$ cells exhibited both pyramidal and non-pyramidal morphologies (data not shown).

Figure 7:
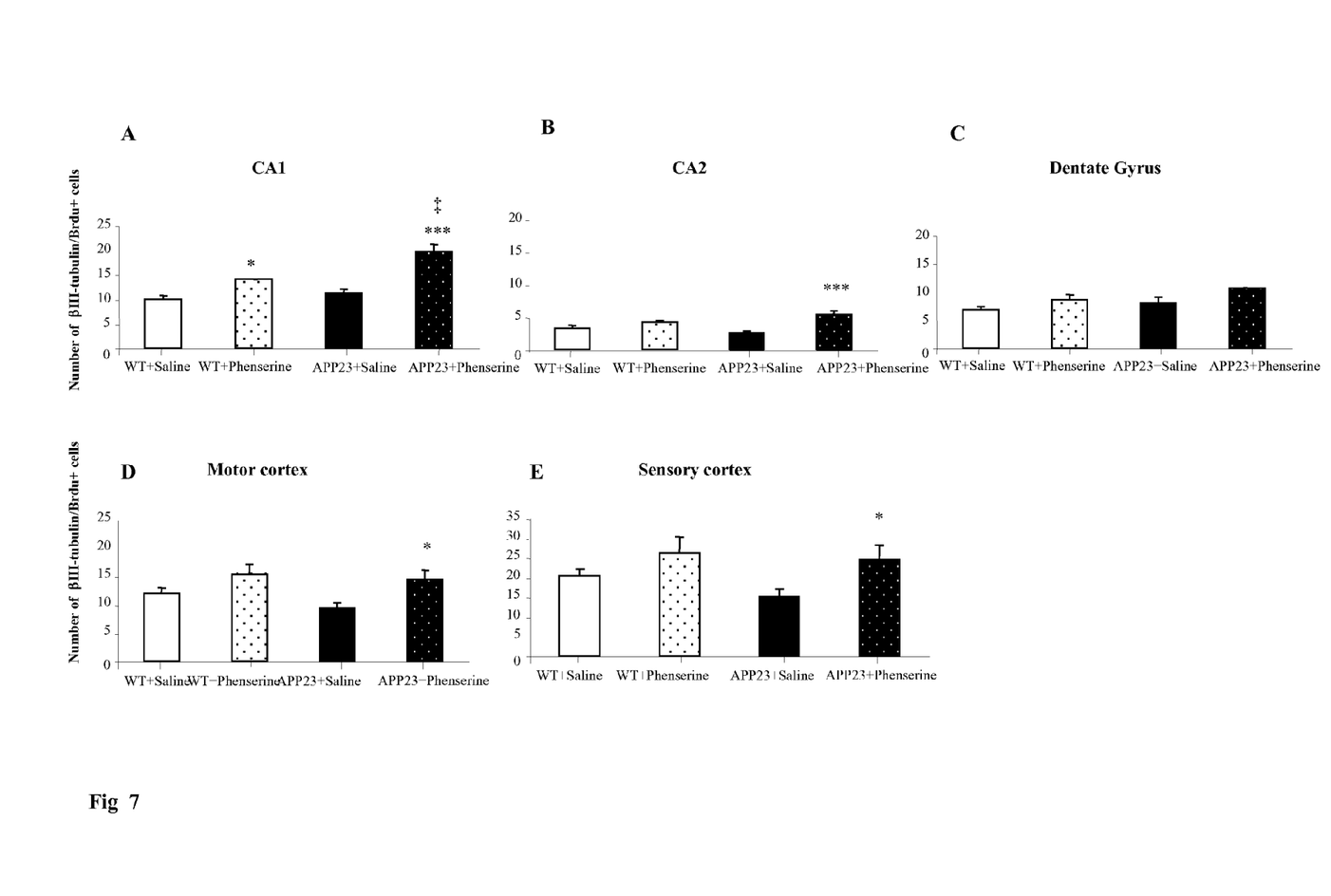
FIG. 7. Immunohistochemical analysis of transplanted HNSC expressing immunoreactivity for neuronal marker βIII-tubulin and Brdu after 6 weeks differentiation in hippocampal and cortical regions of 6-7 months old APP23 and non-transgenic mice that were treated with either saline or phenserine (25 mg/kg). All values are expressed as mean±S.E.M. (n=6-7 within each group), and were obtained by averaging counts of immuno-reactive human-specific neuronal cells in the (A) CA1, (B) CA2, (C) dentate gyrus and (D) motor and (E) sensory cortex, measured bilaterally on four to six alternate sections for each mouse. *** $p<0.0001$; * $p<0.05$ indicates a significant difference from saline treated (Student's unpaired t-test).

We anticipated a reduced neuronal differentiation of transplanted HNSCs in saline treated APP23 mice, based on earlier findings in vitro where more glial differentiation of HNSCs was observed after treatment with sAPP (Kwak et al., 2006). Fewer $BrdU^+/β$-III tubulin$^+$ double immuno-positive cells were detected in the motor and somatosensory cortex of APP23 mice in comparison to wild-type mice (FIG. 7D-E), whereas no significant difference in the number of BrdU⁺/β-III tubulin⁺ double immuno-positive cells was observed in the hippocampal regions of APP23 mice compared to wild-type mice (FIG. 7A-C). Interestingly, we observed a significant increase (ranging from 32% to 112%) in the number of BrdU⁺/β-III tubulin⁺ double immuno-positive cells in the hippocampal CA1 and CA2 ($p<0.0001$), and the motor and the somatosensory cortex ($p<0.05$) of APP 23 mice after (+)-phenserine treatment compared to the number of cells found in APP23 treated with saline (FIG. 7A-B, D-E). A significant ($p<0.05$) increase (40%) in the number of BrdU⁺/β-III tubulin⁺ cells was observed only in the CA1 hippocampal region of wild-type mice treated with (+)-phenserine (FIG. 7A).

REFERENCES

Brannen C, Sugaya K. (2000) In vitro differentiation of multipotent human neural progenitors in serum-free medium. Neuroreport 11:1123-8.

Calhoun M, Burgermeister P, Phinney A, Stalder M, Tolnay M, Wiederhold K, Abramowski D, Sturchler-Pierrat C, Sommer B, Staufenbiel M, Jucker M (1999) Neuronal overexpression of mutant amyloid precursor protein results in prominent deposition of cerebrovascular amyloid. Proc Natl Acad Sci USA 96:14088-93.

Kwak Y D, Brannen, Qu T, Kim M, Dong X, Soba P, Majumdar A, Kaplan A, Beyreuther K, Sugaya K (2006a) Amyloid precursor protein regulates differentiation of human neural stem cells. Stem Cells Dev 15:381-9.

Sturchler-Pierrat C, Abramowski D, Duke M, Wiederhold K, Mistl C, Rothacher S, Ledermann B, Burki K, Frey P, Paganetti P, Waridel C, Calhoun M, Jucker M, Probst A, Staufenbiel M, Sommer B (1997) Two amyloid precursor protein transgenic mouse models with Alzheimer disease-like pathology. Proc Natl Acad Sci USA 94:13287-92.

The invention claimed is:

1. A method of biasing implanted neural stem cells away from differentiation into glial cells, said method comprising administering to a patient in need thereof human neural stem cells to said patient at a site of transplantation, said site of transplantation being in the brain of said patient; and administering a regimen of (+) phenserine, wherein said (+) phenserine is administered according to a regimen such that the site of transplantation comprises an average soluble βAPP concentration of about 0.5 to about 40 nanograms of soluble βAPP per milliliter of tissue or cerebrospinal fluid.

2. The method of claim 1, wherein the human neural stem cells are administered by injecting the human neural stem cells with a syringe, inserting the human neural stem cells with a catheter or surgically implanting the human neural stem cells.

3. The method of claim 2 wherein the human neural stem cells are injected with a syringe into a brain cavity that is fluidly-connected to a target area of neurological deficit.

4. The method of claim 2 wherein the human neural stem cells are inserted with a catheter into a brain cavity that is fluidly-connected to a target area of neurological deficit.

5. The method of claim 2 wherein the human neural stem cells are surgically implanted into a brain cavity that is fluidly-connected to a target area of neurological deficit.

6. The method of claim 1, wherein said (+) phenserine is administered according to a regimen such that an average βAPP concentration of about 1 to 10 nanograms/ml of tissue or cerebrospinal fluid is maintained over a period of at least one day, two days, one week, two weeks, one month, two months, three months, four months, five months, six months or one year.

* * * * *